United States Patent [19]

Cohn et al.

[11] Patent Number: 5,054,493

[45] Date of Patent: Oct. 8, 1991

[54] METHOD FOR DIAGNOSING, MONITORING AND TREATING HYPERTENSION

[75] Inventors: Jay N. Cohn, Minneapolis; Stanley M. Finkelstein, St. Louis Park, both of Minn.

[73] Assignee: Regents of the University of Minnesota, Minneapolis, Minn.

[21] Appl. No.: 652,294

[22] Filed: Feb. 5, 1991

Related U.S. Application Data

[63] Continuation of Ser. No. 250,315, Sep. 28, 1988, abandoned, which is a continuation-in-part of Ser. No. 228,820, Aug. 2, 1988, Pat. No. 4,899,758, which is a continuation of Ser. No. 824,629, Jan. 31, 1986, abandoned.

[51] Int. Cl.$^5$ .............................................. A61B 5/02
[52] U.S. Cl. .................................................... 128/672
[58] Field of Search ............................... 128/672–675; 364/413.02–413.05

[56] References Cited

U.S. PATENT DOCUMENTS 4,562,843 1/1986 Djordjevich et al. ............. 128/672
4,592,364 6/1986 Pinto ................................... 128/672

OTHER PUBLICATIONS

Watt, T. B. et al., "Arterial Pressure Contours Analysis for Estimating Human Vascular Properties", Jrnl of Applied Physics, 1976, pp. 171–176.
Zobel, L. R. et al. "Pressure Pulse Contour Analysis in Determining the Effect of Vasodilator Drugs", Amer. Heart Jrnl. Jul. 1980, vol. 100 No. 1, pp. 81–88.
Aaslid, R. et al., "Cerebral Hemodynamics" (Textbook 1986, Publ. Unknown), pp. 60–85.
"Impaired Systemic Arterial Compliance in Borderline Hypertension" by Hector Ventura, MD, et al., American Heart Journal, vol. 108, No. 1, 1984, pp. 132–136.
"An Evaluation of Large Arteries Compliance in Man" by A. C. Simon et al., American Journal of Physiology, Nov. 1979, vol. 237, No. 5, pp. H550–H554.
"Hemodynamic Mechanisms of and Therapeutic Approach to Systolic Hypertension," A. Simon et al., Journal of Hypertension, Apr. 1987, vol. 5, No. 2, pp. 179–184.
"Post-Synaptic Alpha-Blockade and Brachial Artery Compliance in Essential Hypertension," Jaime Levenson et al., Journal of Hypertension, Feb. 1984, vol. 2, No. 1, pp. 37–41.
"Arterial Compliance in Permanent Essential Hypertension: Preliminary Report" by A. C. Simon et al., Angiology, May 1987, vol. 29, No. 5, pp. 402–409.
"Forearm Arterial Compliance: The Validation of a Plethysmographic Technique for the Measurement of Arterial Compliance," by D. Fitchett et al., Clinical Science, Jul. 1984, vol. 67, No. 1, pp. 69–72.
"Systolic Hypertension in Arterioscherosis Obliterans of the Lower Limbs" by Levenson et al., Clinical and Exper. Hypertension—Theory & Practice, 1982, A4(7), pp. 1059–1072.
Article, "Vascular Impedance in Health, Hypertension, Heart Failure", S. M. Finkelstein et al., (1983) p. 202.
Article, "Vascular Impedance by Pulse Contour/Wind Kessel Analysis (PCWA)", S. M. Finkelstein et al., (1984), p. 27.
Article, "Vasoconstrictor Drug Effects on Vascular Compliance by Pulse Contour Analysis," J. Mack, B. A. et al., (Nov. 1987).

(List continued on next page.)

*Primary Examiner*—Francis Jaworski
*Attorney, Agent, or Firm*—Merchant, Gould, Smith, Edell, Welter & Schmidt

[57] ABSTRACT

A method for diagnosing, monitoring and treating hypertension uses the parameter $C_2$ of the modified Windkessel model as an indication of the hypertensive disease condition. Apparatus for determining the parameter $C_2$ (i.e. distal vascular compliance) of the modified Windkessel model includes means for obtaining a pressure pulse contour and a cardiac output value and for determining the model parameters.

26 Claims, 5 Drawing Sheets

OTHER PUBLICATIONS

Article, "Reduced Arterial Compliance in Hypertension," W. I. Feske et al. (Sep. 1988) p. 343.

Article, "Vascular Compliance Changes During the Progression of Hypertension in Dogs", J. E. Mock et al., (Sep. 1988), p. 360.

Article, "Vascular Compliance After Nitroprusside in Hypertension," W. Feske, B. A. et al. (Mar. 1988), pp. 277–280.

Article, "ACE Inhibition and Brachial Artery Hemodynamics in Hypertension," A. Simon et al., (1984) pp. 2435–2465.

Article, "Vasodilator Effects on Vascular Impedance Characteristics," S. M. Finkelstein et al. (1979) p. 991.

Abstract of Article, "Evaluation of a Pulse Contour Technique for Measuring Arterial Elasticity", V. R. Collins et al. (1980).

Article, "Vascular Impedance Response to Vasodilator Drugs", S. M. Finkelstein et al. (1981), p. 346.

Abstract, "Evidence for Abnormal Vascular Compliance by Pulse Contour Analysis in Congestive Heart Failure," S. M. Finkelstein et al. (1982).

Article, "Vascular Hemodynamic Impedance Measurement," S. M. Finkelstein & V. R. Collins, (1982), pp. 401–418.

Article, "Vascular Impedance Methodology in Congestive Heart Failure," S. M. Finkelstein et al. (1982), p. 143.

Article, "Measurment of Vascular Compliance as a Guide to Vasoconstrictor and Vasodilator Stimuli", J. N. Cohn et al., (1983), p. 189.

Article, "Estimation of Fore Arm Arterial Compliance . . . Using a Pulsed Doppler Device and a First Order Arterial Model During Diastole", A. Simon et al., (1983) pp. 331–338.

Article, "Impedance Response to Nitroprusside in Heart Failure", S. M. Finkelstein et al. (1984), p. 259.

Article, "Response of Vascular Compliance to Converting Enzyme Inhibitors in Heart Failure," S. M. Finkelstein et al. (1985).

Article, "Ventricular/Vascular Interaction in Patients with Mild Systemic Hypertension and Normal Peripheral Resistance," W. P. Nichols, Ph.D et al. (1986), pp. 455–462.

Abstract, "Vascular Compliance Response to Converting Enzyme Inhibitors in Heart Failure", S. M. Finkelstein et al. (1987).

Abstract, "Vasoconstrictor-Mediated Reduction in Vascular Compliance Assessed by Pulse-Contour-Analysis (PCA)", J. E. Mock et al. (1987).

Article, "Effects of a Lack of Aortic 'Winkessel' Properties on the Left Ventricle," H. Maeta, M. D. & Mittori, M. D. (1985) pp. 232–237.

Article, "Stroke Volume—Pulse Pressure Relationships in Borderline Hypertension: A Possible Indicator of Deceased Arterial Compliance", Ferguson et al. (1984), pp. 397–399.

Article, "Reversion of Cardiac Hypertrophy and Reduced Arterial Compliance After Converting Enzyme Inhibition in Essential Hypertension," R. G. Asmar et al. (1988).

Article, "Hypertension in the Elderly", J. R. Sowers, M.D. (1987), pp. 1–8.

Article, "Treatment for One Year with Peridopril: Effect on Cardiac Mass and Arterial Compliance in Essential Hypertension,", R. G. Asmar et al. (1988), pp. 533–539.

Article: "Arterial Pressure Pulse Contour Analysis Via a Mathematical Model for the Clinical Quantification of Human Vascular Properties," by Roger Goldwyn & Thomas B. Watt, Jr. Transactions of Bio-Medical Engineering vol. BME 14, #1, Jan. 1967.

Article, "Arterial Pressure Contour Analysis for Estimating Human Vascular Properties" Thomas Watt & Clarles Burrus, *Journal of Applied Physiology* 1976.

Article, "Vascular Hemodynamic Impedance in Cogestive Heart Failure" by Finkelstein et al., *American Journal of Cardiology*, 1985.

Article "Vascular Compliance in Congestive Heart Failure" by Finkelstein et al., Proceedings of Seventh Annual Conference of the IEEE Engineering in Medical and Biology Society, Chicago, Ill., Sep. 27–30, 1985.

Article "Pressure Pulse Contour Analysis in Determining the Effect of Vasodialator Drugs on Vascular Hemodynamic Impedance Characteristics in Dogs", by Larry R. Zobel et al., American Heart Journal, Jul. 1980, vol. 100, No. 1.

Article, "Arterial Vascular Compliance Response to (List continued on next page.)

OTHER PUBLICATIONS

Exercise in Hypertension," by William Feske et al., *Biomedical Science Instrument*, vol. 24, 1988.

Article, "Vascular Compliance Changes in Hypertensive Dogs During Nitroprusside Infusion as Measured by Pulse-Contour-Analysis" by James Mock et al., *Modern Pathology* vol. 1, No. 6, 1988.

Article, "Effects of Calcium Channel Blockade on Cardiac Repercussions of Long-Standing Hypertension" by Franz Messerli, *Journal of Cardiovascular Pharmacology*, vol. 12 (Suppl. 6) 1988.

Article, "Current Status and Prospects for Arterial Hypertension Research in the Soviet Union," by Igor Shkhuatsabaya *Health Psychology* 1988, vol. 7, (Supp.).

Article, "Arterial and Venous Compliance in Sustained Essential Hypertension," M. E. Safar et al., *Hypertension*, Aug. 1987.

Article, "Vascular Distensbility and Vascular Surgery", by J. M. Van de Water et al., *American Surgery*, Dec. 1985.

Article, "Enhanced Brachial Artery Compliance Following Perindopril in Essential Hypertension," by R. G. Asmar, *American Journal of Hypertension*, Jul. 1988 (3 pt. 3).

Article, "Pulse Pressure in Sustained Essential Hypertension: A Hemodynamic Study," by M. E. Safar et al., *Journal of Hypertension*, Apr. 1987, vol. 5, No. 2.

Article, "Hemodynamic Basis of Early Modification of the Large Arteries in Borderline Hypertension," by A. Simon, *Journal of Hypertension*, Apr., 1987, vol. 5, No. 2.

Article, "Changes in Arterial Distensibility Produced by Converting Enzyme Inhibitors in Hypertensive Humans," by M. E. Safar et al., *Clinical and Experimental Thoery & Practice*, 1987.

Article, "Estimation of Total Arterial Compliance: An Improved Method and Evaluation of Current Methods", Z. Liu, et al. *American Journal of Physiology*, Sep. 1986, #251 (3 pt. 2).

Article, "Noninvasive Determination of Arterial Compliance", by S. Chai, et al., *Medical Engineering Comput.*, Jul. 1983, vol. 21, No. 4.

Article, "Vascular Impedance in Studies of Arterial and Cardiac Function", M. F. O'Rourke, *Physiological Review*, Apr., 1982, vol. 62, No. 2.

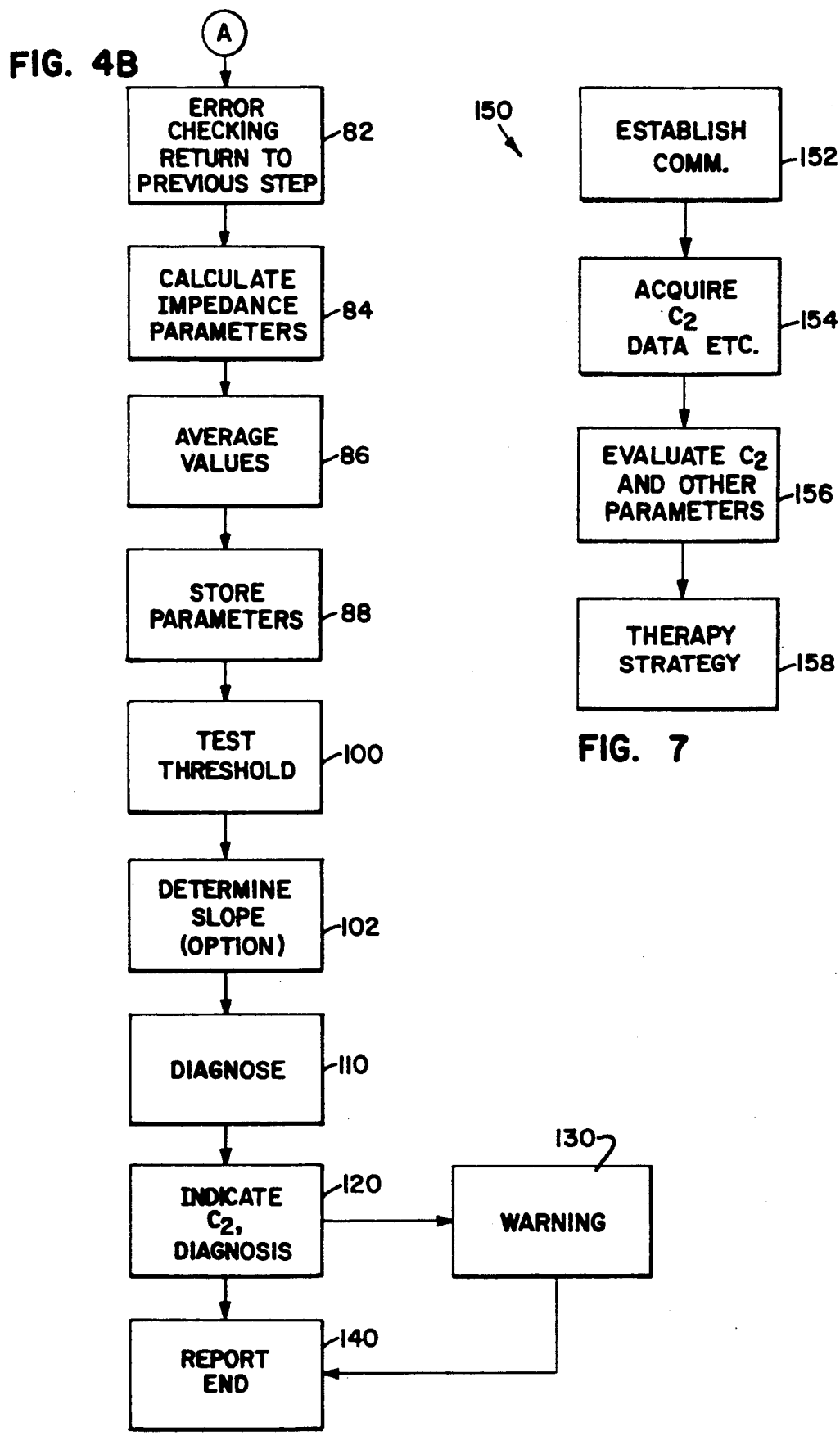

METHOD FOR DIAGNOSING, MONITORING AND TREATING HYPERTENSION

This invention was made with Government support under Grant No. 5P01-HL 1787107 and 1P01-HL 32427. The Government has certain rights in the invention.

CONTINUATION DATA

This is a continuation of application Ser. No. 07/250,315 filed Sept. 28, 1988, and now abandoned, which is a continuation-in-part of U.S. application Ser. No. 228,820, filed Aug. 2, 1988, entitled "Method & Apparatus for Monitoring and Diagnosing Hypertension and Congestive Heart Failure" by Finkelstein and Cohn, now U.S. Pat. No. which is a continuation of U.S. application Ser. No. 824,629, filed Jan. 31, 1986, and now abandoned. The entire disclosure of Ser. No. 228,820 is hereby incorporated by reference herein.

TECHNICAL FIELD OF THE INVENTION

The present invention relates generally to the fields of cardiac and circulatory medicine, and more particularly to the medical disorder of hypertension.

BACKGROUND OF THE INVENTION

Hypertension is defined as abnormally elevated blood pressure. More specifically, when a person under conditions of rest consistently has a blood pressure that exceeds 145/90 (systole/diastole), the person is said to have high blood pressure or hypertension. It is currently believed that over fifty million people in the United States have hypertension and fifteen to twenty percent of all deaths in people over fifty years of age occur as a direct or indirect result of hypertension. Actuarial statistics show that the disability and mortality rates of hypertensive persons are higher for each age bracket than for persons with normal blood pressure. Specific ailments attributable to hypertension include heart failure, myocardial infarction, rupture or thrombus of the blood vessels in the brain and kidney damage.

Despite the prevalence of hypertension and its potentially severe consequences to health, its detection, treatment and diagnosis remains entirely dependent on blood pressure measurements. However, the presence of high blood pressure in a patient at any given time only establishes that the patient's blood pressure at that moment is high; it says nothing about the patient's underlying medical condition. Substantial transient variations in blood pressure, for example as caused by digestion, exercise, posture, circadian rhythms and emotional states, occur on a regular basis in any individual. Thus, it is not possible to tell, absent continuous measurements and periodic followup over time, whether a hypertensive state is a function of a transient condition or is of a chronic nature. Blood pressure measurements in and of themselves do not reveal the presence of the hypertensive disease condition, which can be defined as the process or presence of underlying physical changes in the human body which result in the state of hypertension.

The inability to measure or detect the hypertensive disease condition as opposed to merely its ultimate effects, i.e. the state of elevated blood pressure, is a glaring and problematic deficiency in the diagnosis, treatment and care of hypertensive individuals. This deficiency manifests itself in various ways. For one, it can result in unnecessary and undesirable antihypertensive treatment for individuals who are diagnosed hypertensive due to elevated blood pressure but who may not have the hypertensive disease condition. For instance, many healthy individuals may exhibit blood pressures which are classified as hypertensive, or borderline hypertensive, according to the statistical norm of 145/90. Administering antihypertensive therapy to such healthy patients and subjecting them to its potentially undesirable side effects is clearly ill advised. On the other hand, certain individuals may exhibit normal blood pressure as it is statistically defined, yet suffer from the underlying hypertensive disease condition. These individuals may benefit from antihypertensive therapy yet it would not, according to current practices, be prescribed for them.

Moreover, without knowledge of underlying physical abnormalities the severity or intractability of a particular case of hypertension cannot be determined without extended monitoring of the response of a patient to treatment. Furthermore, a predisposition to development of hypertension is impossible to ascertain other than by predictions made from the medical history of a patient's family. Thus, there is a strong need to develop diagnostic tools for detecting and measuring the hypertensive disease condition.

A considerable amount of research has been conducted into the causes and effects of hypertension in humans. Most of this research has focussed on the properties of the human vasculature which affect and control blood flow and blood pressure. For example, in the mid 1970's Thomas B. Watt, Jr. and Charles S. Burrus investigated the use of the modified Windkessel model to quantify properties of the human vascular system. The results of this investigation were published in their article entitled "Arterial Pressure Contour Analysis for Estimating Human Vascular Properties" *Journal of Applied Physiology* (1976) 40(2): 171-176. This article describes the experimental procedures and techniques used by Watt and Burrus to investigate the Windkessel model, and presents test data supporting their conclusions.

The modified Windkessel model investigated by Watt and Burrus is a third-order electrical model of the arterial system. The model includes two capacitive elements, $C_1$ and $C_2$, an inductance component L and a resistance component R. Hypothetically, $C_1$ corresponds to the "proximal vascular compliance", defined as the lumped elastic compliance of major arteries, $C_2$ to that of "distal vascular compliance", defined as the vascular compliance of smaller peripheral arteries and arterioles, L to the lumped inertia of major blood columns and R to the total vascular resistance assumed to be located primarily in arterioles and capillaries. These quantities all portray gross effective mechanical behavior of complex networks of blood-filled vessels.

As part of their investigation, Watt and Burrus determined the values for the model parameters for fifteen normal subjects and for comparison four hypertensive patients. The fifteen normal subjects studied were young adult males, mostly graduate students, who satisfied clinical criteria of cardiovascular normalcy. The data obtained showed that distal compliance was distinctly lower in the hypertensive than in the normal subjects suggesting that the hypertensive patients had less compliant distal vessels than the normal subjects.

While the minimal data reported by Watt and Burrus suggested a connection between hypertension and reduced distal compliance measurements (as quantified by the parameter $C_2$) the investigation was statistically inconclusive for want of a sufficient study population of hypertensive subjects. The study was also medically inconclusive for want of data showing a continuum of blood pressure measurements and corresponding distal compliance measurements from which meaningful conclusions as to the relationship between blood pressure and distal compliance could be drawn. In any event, the Watt and Burrus findings did not lead to further research on the relationship of distal compliance to hypertension. In fact, as explained below, all of the known research conducted since the Watt and Burrus findings were published (with the exception of the Applicants' publications) has focussed on the relationship between proximal compliance and hypertension. Thus, it is clear that the findings of Watt and Burrus did not suggest to one of ordinary skill in the art that distal compliance could be an important and clinically useful marker of the hypertensive disease condition. In fact, it would appear that just the opposite was true.

As noted above, despite the findings reported by Watt and Burrus in their 1976 paper, virtually all hypertension research conducted since that time to date has focussed on studying the properties of the large, proximal arteries and the relationship of the properties of these arteries, in particular their compliance, to hypertension. For example, the research group of Simon, Levenson and Safar et al. has conducted a number of studies on the relationship between the compliance of large arteries and hypertension. (See, for example, A. Simon, J. Levenson, J. Bouthier, and B. Maarek, "Haemodynamic Basis of Early Modifications of the Large Arteries in Borderline Hypertension", (J-Hypertens., 1987 Apr. 5(2); P. 179–84); M. E. Safar and G. M. London, "Arterial and Venous Compliance in Sustained Essential Hypertension", (Hypertension, 1987 Aug. 10(2); P. 133–9); A. C. Simon, J. A. Levenson and M. E. Safar, "Hemodynamic Mechanisms of and Therapeutic Approach to Systolic Hypertension", (J-Cardiovasc. Pharmacol, 1985, 7 Suppl. 2; P. S22-7); A. C. Simon, J. A. Levenson, A. M. Safar, J. D. Bouthier, and M. E. Safar, "ACE Inhibition and Brachial Artery Haemodynamics in Hypertension", (Br. J. Clin. Pharmacol. 1984, 18 Suppl. 2; P. 243S–247S); J. Levenson, A. C. Simon, J. D. Bouthier, A. Benetos and M. E. Safar, "Post-Synaptic Alpha-Blockade and Brachial Artery Compliance in Essential Hypertension", (J. Hypertens. 1984 Feb. 2(1); P. 37–41); D. Fitchett, J. D. Bouthier, A. C. Simon, J. A. Levenson, and M. E. Safar, "Forearm Arterial Compliance: The Validation of a Plethysmographic Technique for the Measurement of Arterial Compliance", (Clin. Sci. 1984 Jul. 67(1); P. 69–72); J. A. Levenson, A. C. Simon, M. E. Safar, J. N. Fiessinger, and E. M. Housset, "Systolic Hypertension in Arteriosclerosis Obliterans of the Lower Limbs", (Clin. Exp. Hypertens. [A] 1982, 4(7); P. 1059–72); A. C. Simon, M. E. Safar, J. A. Levenson, G. M. London, B. I. Levy and N. P. Chau, "An Evaluation of Large Arteries Compliance in Man", (Am. J. Physiol. 1979 Nov. 237(5); P. H550-4); and A. C. Simon, B. I. Levy, Y. A. Weiss, M. A. Kheder, J. M. Levenson and M. E. Safar, "Arterial Compliance in Permanent Essential Hypertension: Preliminary Report", (Angiology, 1987 May, 29(5); P. 402-9).

In many of the above noted studies the Simon group characterized the compliance of the large arteries by use of a first order resistance-capacitance (RC) electrical model. Using this model the Simon group found that the compliance of the large arteries was decreased in patients with essential hypertension. Similar results have been reported by others conducting similar research. A good representation of these findings are found, for instance, in the publication of Ventura et al., entitled, "Impaired Systemic Arterial Compliance in Borderline Hypertension", (Am Heart J 108: 132, 1984).

While both the Simon group and Ventura et al. reported that the compliance of the large arteries appeared to be reduced in hypertensive patients, the difference in the compliance of large arteries between healthy and hypertensive patients is not great enough to make this compliance measurement clinically useful as a diagnostic tool for identifying patients with the hypertensive disease condition. The above-referenced publication of Ventura et al. shows several plots of compliance measurements for healthy vs. hypertensive groups. As can be seen from those plots, even though the average compliance measurement for healthy patients differs from that of hypertensive patients, many healthy, normotensive patients, who did not have a hypertensive disease condition and would have had anormal distal compliance, had large-artery compliance measurements in the same range as those found in a number of hypertensive patients. As a result, there is no distinct and clinically useful line dividing compliance measurements found in hypertensive patients from those found in normotensive patients. Thus, the compliance of large arteries is not a sensitive and discriminating enough marker of the hypertensive disease condition to be clinically useful.

Accordingly, despite years of research there is still a need for a clinically useful diagnostic tool for detecting and measuring the hypertensive disease condition. As set forth below, the present invention at last provides such a tool.

SUMMARY OF THE INVENTION

The present invention provides method for the detection, diagnosis, monitoring and treatment of hypertension. More specifically, the present invention calls for measuring the distal compliance of a patient's vascular system and for using the measured compliance as a marker of the hypertensive disease condition. According to one aspect of the invention, the parameter $C_2$ of the modified Windkessel model is used as a measure of distal compliance.

BRIEF DESCRIPTION OF THE DRAWING

FIGS. 4a and 4b comprise a schematic flow chart of the software of the present invention;

FIG. 7 is a schematic diagram of the software to be used in the clinic computer according to the present invention.

DETAILED DESCRIPTION OF THE INVENTION

Figure 1:
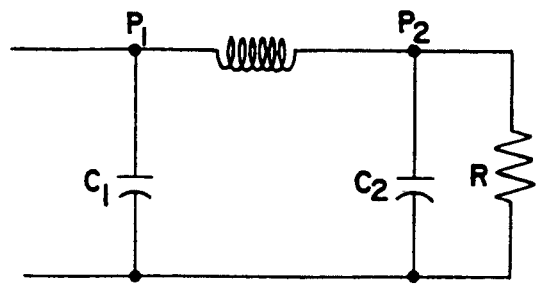
FIG. 1 is a drawing of the modified Windkessel model of the human vasculature.

The present invention is based on the results of a study of the vasculature of a group of hypertensive patients and a group of normotensive patients. The hypertensive patients all had a history of elevated blood pressure with blood pressure cuff measurements exceeding 145/90 at the time of the study. The normotensive subjects all had cuff blood pressure measurements below 145/90. The modified Windkessel model of the arterial system was used to characterize the vasculature of each subject. The modified Windkessel model of the arterial system is shown in FIG. 1. In the model, $C_1$=proximal compliance (ml/mm Hg); $C_2$=distal compliance (ml/mm Hg); L=inertence (mm Hg/ml/s(2)); $P_1$=proximal arterial (aortic) pressure (mm Hg); $P_2$=distal arterial (brachial) pressure (mm Hg); and R=peripheral resistance (dynes s cm$^{-5}$).

Blood pressure waveforms for each patient in the study were recorded from the brachial artery using an 18-gauge, 2 inch Teflon ® catheter connected to a Statham P23Db pressure transducer. This catheter-transducer system has an undamped natural frequency higher than 25 Hz and a damping coefficient less than 0.5 as measured by balloon pop in the laboratory. This frequency response is adequate for the pulse-contour technique for obtaining measurements of the parameters of the modified Windkessel model. Aortic valve closure was determined from heart sounds from the upper left sternal border. The beginning of the second heart sound ($S_2$) indicated the onset of diastole, and the upstroke of the brachial artery pulse was used to mark the end of diastole. A thermodilution balloon floation catheter was positioned in the pulmonary artery after percutaneous insertion into a brachial vein in the patient. Cardiac output was determined in triplicate by thermodilution. In normal subjects cardiac output was measured by the thoracic impedance using the Minnesota Impedance Cardiograph Model 30413.

Blood pressure waveforms were recorded for 30 seconds for each subject in a supine position, after at least 60 minutes supine rest after catheter positioning. All hemodynamic data were recorded on both paper and magnetic tape. Data were digitized using 12-bit analog to digital converter operating at 200 samples per second per channel. Digitized data were saved on disc for subsequent beat marking, signal processing and pulse-contour analysis. The onset and end of diastole for the brachial artery pressure waveform were marked on six consecutive beats and the modified Gauss-Newton parameter-estimating algorithm was run on each marked beat. Each group of six consecutive beats was selected manually from each 30-second record choosing the group with the most noise-free pressure and phonocardiogram signals as viewed by the operator. The diastolic waveform for each beat can be represented most generally as the third-order function:

$$P(t) = A_1 e^{-A_2 t} + A_3 e^{-A_4 t} \cos(A_5 t + A_6)$$

The parameter-estimating algorithm calculated the optimal values for the $A_i$(i=1 ... 6) so that the estimated function fit the observed data with a minimum least square error. These $A_i$ coefficients, mean pressure and cardiac output values were then used to determine the circuit elements (compliance, inertence and resistance) in the modified Windkessel model of the vasculature, in which the measure of brachial arteriole pressure was taken as $P_2(t)$. Heart rate, pulse velocity and wave reflections do not figure directly into determination of the circuit parameters. The results for each six consecutive beats were averaged and the mean values were used in the statistical data analysis. Further details on the pulse-contour analysis of the study method are described below.

Figure 2:
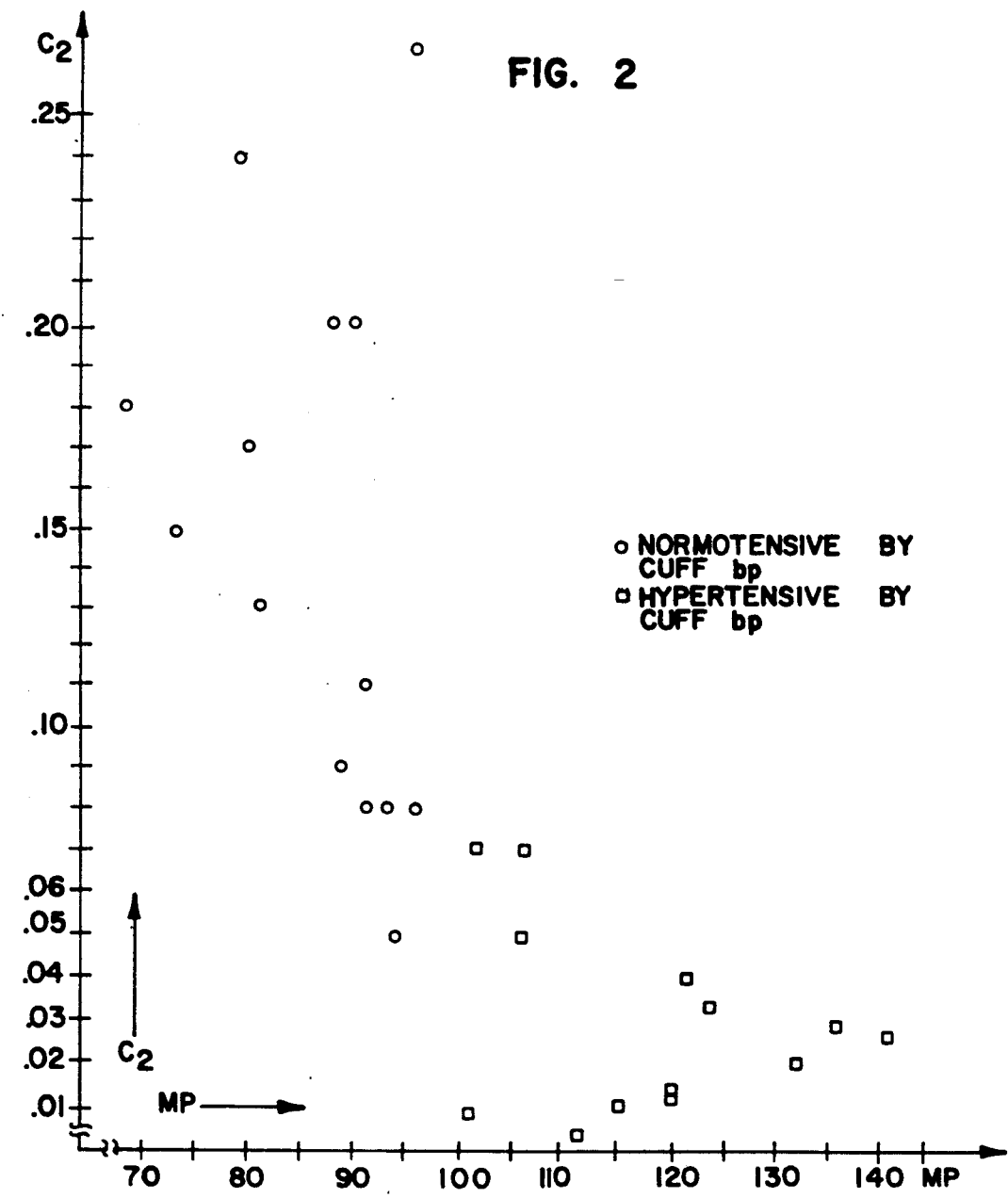
FIG. 2 is a plot of mean arterial pressure (mp) versus $C_2$ for a group of normotensive subjects and a group of hypertensive patients as diagnosed by blood pressure cuff (sphygmomanometer) measurements.

FIG. 2 shows the plotting of the mean arterial pressure (mp) versus distal compliance as quantified by the measured $C_2$ parameter for all of the subjects in the study, with the normotensive patients represented by open circles and the hypertensive patients represented by squares. For the sake of comparison, it is noted that mean arterial pressure is approximately equal to the diastolic pressure measurement plus one-third the difference between the systolic and diastolic measurements. For example, a 145/90 cuff measurement would equate to a mean arterial pressure of about 108 mm Hg.

As shown by the plot, $C_2$ varies widely in normotensive subjects but is consistently reduced in subjects with hypertension. The plot also shows a generally linear decrease in the measured $C_2$ distal compliance value with increase in mean arterial pressure. The results of this study thus establish: 1) hypertensive subjects have consistently reduced distal compliance; 2) distal compliance is independent of blood pressure, i.e. two persons with the same blood pressure can have widely varying distal compliance, particularly among normotensive subjects; 3) there is a distinct division between distal compliance measurements for normotensive and hypertensive patients; and 4) the underlying physical condition of distal compliance, as quantified by Cz measurements, can be used as a marker of the hypertensive disease condition. The study also supports the following inferences: 1) a normotensive or borderline hypertensive patient with a high $C_2$ value is unlikely to develop the hypertensive disease condition and its associated chronic hypertension; and 2) normotensive or borderline hypertensive subjects with reduced $C_2$ values are more likely to develop chronic hypertension than normotensive or borderline hypertensive subjects with high $C_2$ values.

The results of the study described and discussed above thus establish that distal compliance is a specific marker for the hypertensive disease condition and that diagnosis and drug therapy of the disease called hypertension can be made more precise by measurement of $C_2$ than by measurement of cuff blood pressure alone. As noted above, the blood pressure may vary widely and may be normal on many occasions in some patients who have the hypertensive disease condition and may be high on occasions in patients who do not have the hypertensive disease condition. Thus, the measurement of blood pressure alone is not useful in identifying patients who have the hypertensive disease condition. However, the $C_2$ measurement will be reduced in patients who have the hypertensive disease condition regardless of blood pressure and will be elevated in patients who do not have the hypertensive disease condition regardless of their blood pressure. Therefore, distal compliance $C_2$ measurements can serve the unique purpose of identifying the hypertensive disease condition, particularly in patients with borderline blood pressures which may sometimes be normal and sometimes be elevated.

The use of distal compliance as a marker for the hypertensive disease condition has several important clinical applications, certain of which are specified as follows. For one, distal compliance measurements can be used to exclude from unnecessary antihypertensive therapy patients whose blood pressure may periodically be elevated but who do not have the hypertensive disease condition. To this end the present invention provides a method for determining treatment for a patient with borderline hypertension comprising: 1) determining for the patient a measure of distal compliance; and 2) administering medications known to raise distal compliance (i.e. make the vessels more elastic) if said distal compliance is less than a first predetermined diagnostic threshold. Alternatively, or in addition, the patient can be identified as one not likely to benefit from administration of medication which increases distal compliance if the patient's distal compliance is greater than a predetermined diagnostic threshold. According to this method, a patient is defined as borderline hypertensive if their blood pressure is sometimes elevated and in the hypertensive range but is at other times normotensive. By use of this method, many patients can be spared from the side effects and inconvenience of antihypertensive drug therapy, and, moreover, the cost of their medical care can be reduced.

Another application of the principles of the present invention is the use of distal compliance measurements for identifying the hypertensive disease condition and/or quantifying its severity. This method comprises the steps of: 1) determining for the patient a measure of distal compliance; 2) diagnosing the patient as having the hypertensive disease condition if distal compliance is less than a first predetermined diagnostic threshold; and 3) diagnosing the patient as not having the hypertensive disease condition if distal compliance is greater than said first threshold, or, in the alternative, a second predetermined diagnostic threshold. According to one variant of this method, persons determined to be hypertensive by cuff blood pressure measurements can be further tested to determine their distal compliance. If their distal compliance is above a certain level, the person can be diagnosed as not likely to benefit from antihypertensive drug therapy designed to raise distal compliance and, moreover, as perhaps only suffering from a transient elevation of blood pressure. According to another variant of this method, the distal compliance measures can be used to assess the severity and/or the likelihood that a case of hypertension will respond to treatment. For instance, persons with only marginally high blood pressure but having very poor distal compliance, e.g. $C_2$ measurements below 0.02 ml/mm Hg, might be classified as having a severe hypertensive disease condition (although they are only mildly hypertensive) whereby it would be known that the patient requires extensive therapy and followup. Moreover, it would be known that such a patient may greatly benefit from antihypertensive drug therapy to raise their distal compliance.

According to yet another application of the discovery of the present invention, there is provided a method for early detection of the development of the hypertensive disease condition comprising the steps of: 1) determining for the patient a measure of distal compliance; 2) repeating step 1) over a period of time and charting the course of distal compliance; and 3) diagnosing a movement toward the onset of the hypertensive disease condition if the course of charted distal compliance is trending downwardly indicating deteriorating distal compliance.

Another application of the discovery of the present invention comprises a method for monitoring the progress of the hypertensive disease condition comprising the steps of: 1) determining for the patient a measure of distal compliance; 2) repeating step 1) over a period of time and charting the course of distal compliance; and 3) diagnosing the progress of the hypertensive disease condition based on said charted course, said progress being diagnosed as unchanged if said measures stay substantially unchanged over time, worsening if said measures decrease over time indicating decreasing distal compliance, and improving if said measures increase over time indicating increasing distal compliance.

Thus, there has been described above several specific applications of the principles of the present invention to use distal compliance as a marker of the hypertensive disease condition. These applications provide methods for detecting, diagnosing, monitoring and treating the hypertensive disease condition. In the specific methods outlined above the present invention contemplates using the $C_2$ parameter of the modified Windkessel Model as a measure of distal compliance. It shall be understood, however, that other measures of distal compliance, if developed, would most likely also work in applying the various methods and principles of the present invention contemplated herein. Moreover, it shall be understood that "distal compliance" as that term is used herein is in essence defined as the physiologic attribute measured by the $C_2$ parameter of the modified Windkessel Model. Since the parameter $C_2$ of the modified Windkessel Model only represents the compliance of smaller peripheral arteries and arterioles in theory, it is possible that the parameter $C_2$ is influenced by other aspects of the vascular system which are not presently appreciated, and which if known might lead to a more exact measure of the physiological bases of the hypertensive disease condition. Accordingly, it shall be understood that the use of such more exact measures, if developed, are within the scope of the methods and principles of the present invention.

According to the results of the study disclosed herein, a $C_2$ value up about 0.05 ml/mm Hg defines a diagnostic threshold value below which there is a high degree of certainty that the patient is suffering from the hypertensive disease condition. However, the exact $C_2$ value selected as choice. For instance, it may be desirable to diagnose borderline hypertensive patients with $C_2$ measurements below a value such as 0.12 ml/mm Hg as likely to benefit from antihypertensive therapy directed toward raising distal compliance. In such cases antihypertensive therapy might reduce the patient's prevailing blood pressure level so that transient increases in blood pressure, as for example caused by stress, would not exceed dangerous levels whereby, for instance, a blood vessel may rupture and result in a stroke. Moreover, as contemplated by the methods described above, it may be desirable to choose a first diagnostic threshold value below which the hypertensive disease condition is diagnosed and a second, different threshold value above which the hypertensive disease condition is diagnosed as absent. For instance, the study results presented herein indicate that a $C_2$ value of 0.08 ml/mm Hg and above would indicate with a high degree of certainty that the hypertensive disease condition was absent. Patients with values between the thresholds could be diagnosed as borderline cases.

Figure 3:
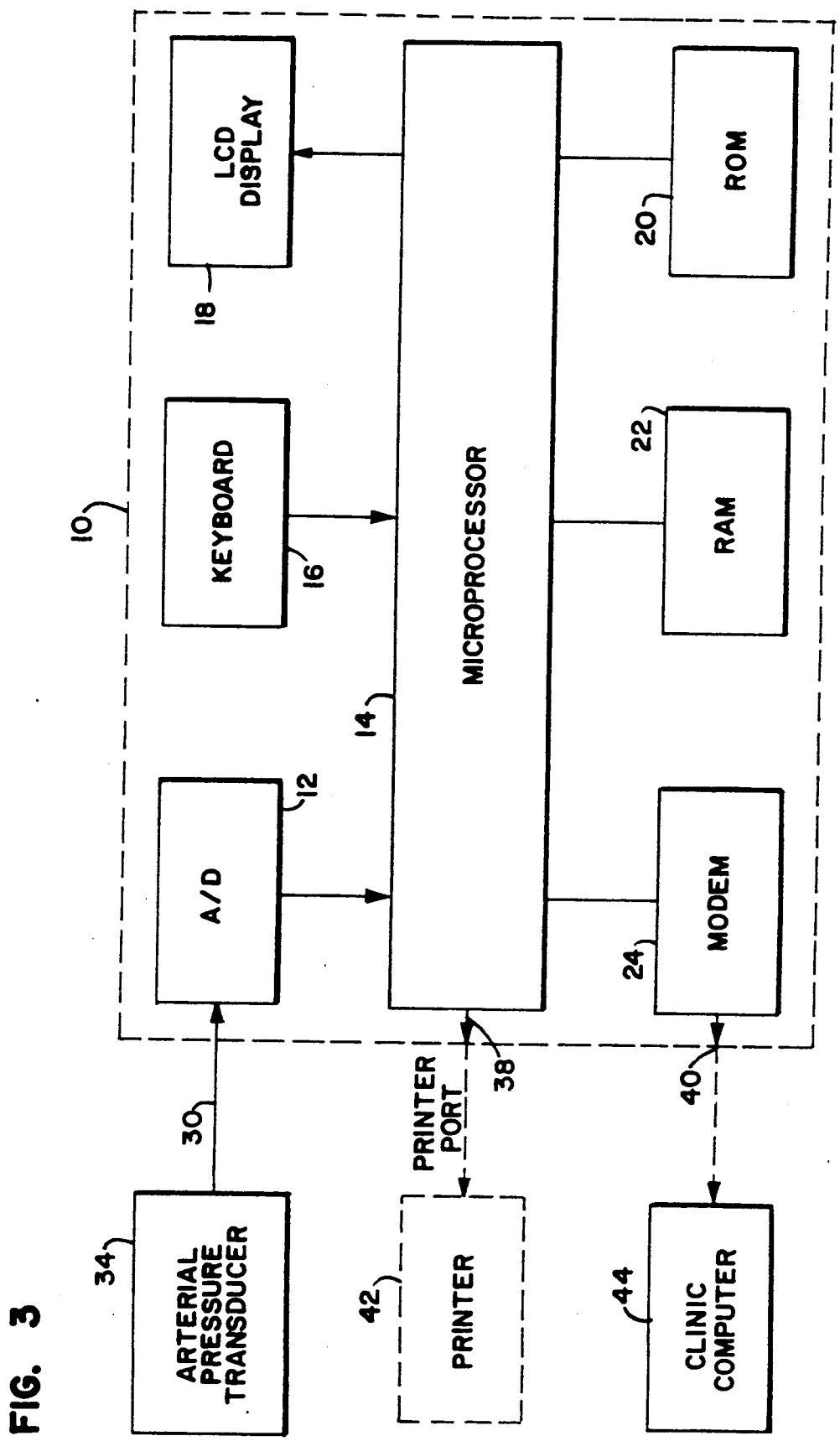
FIG. 3 is a schematic block diagram of the monitor according to the present invention.

The present invention also provides apparatus for measuring, monitoring and diagnosing the hypertensive disease condition. The vascular compliance apparatus 10 according to the present invention is shown in schematic block diagram form in FIG. 3. The monitor 10 includes an analog to digital convertor (A/D) 12, preferably 12-bit, a microprocessor unit 14, for instance a 6502 model, a keyboard input 16, display 18, ROM 20, RAM 22 and modem 24. An input port 30 is provided to receive analog signal input from an arterial pressure transducer 34. A printer output port 38 and a telephone port 40 are provided from microprocessor 14 and modem 24, respectively.

Transducer 34 is preferably a Statham P23Db pressure transducer, and is preferably connected from its operative position in a brachial artery to part 30 through an 18-gauge, 2-inch Teflon catheter. This catheter-transducer system has an undamped natural frequency higher than 25 HZ and a damping coefficient less that 0.5, providing an acceptable frequency response. It shall be understood, however, that while the brachial artery is preferred, other arterial locations for obtaining the pressure pulse contour could be substituted. Moreover, it is contemplated that a non-invasive method for measuring arterial pressure waves could also be used.

Figure 4A:
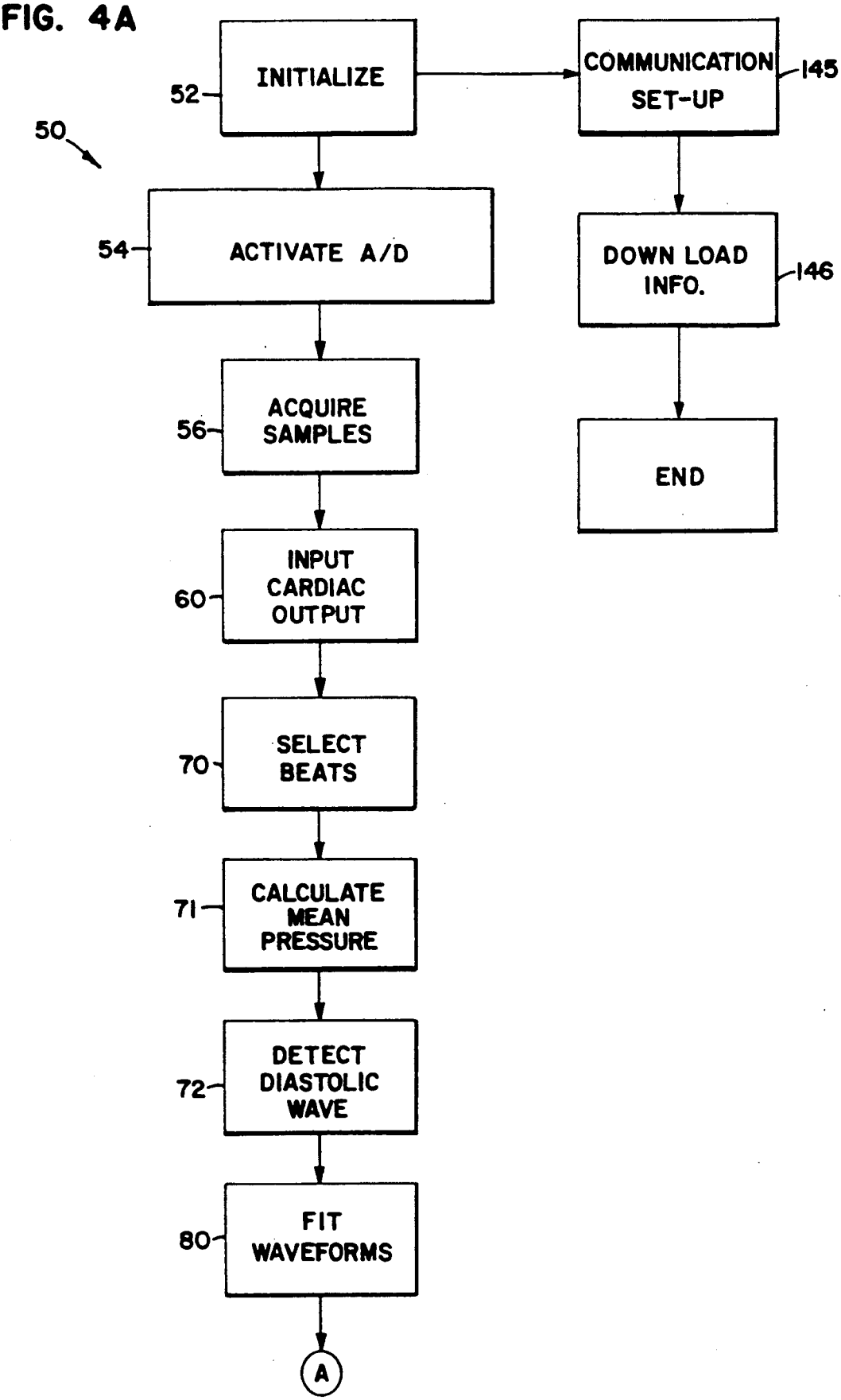

The software component 50 of the monitor 10 is illustrated in block diagram flow-chart form in FIGS. 4a and b. Software 10 is preferably maintained in ROM 20 and is referenced by microprocessor 14. Alternatively, software 50 could be stored in magnetic form on a floppy disk connected to be accessed by monitor 10. Generally speaking, software 50 runs on microprocessor 14 to control the acquisition of artery pressure pulse data, and to process, analyze and diagnose the acquired data.

Figure 5:
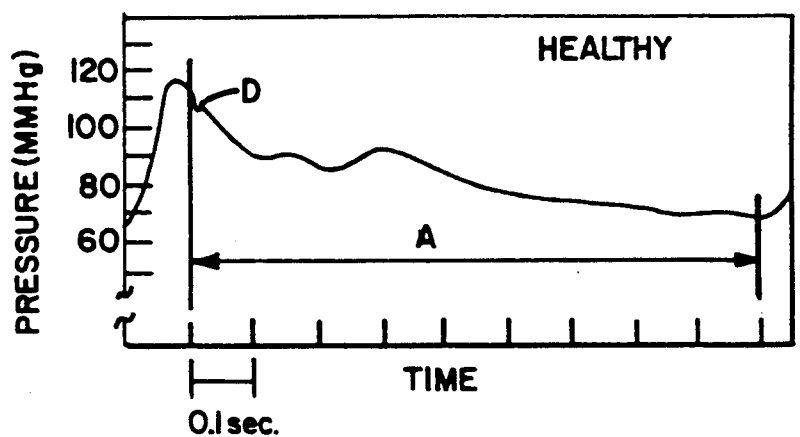
FIG. 5 is an illustrative example of typical arterial pulse contours in healthy patients.
Figure 6:
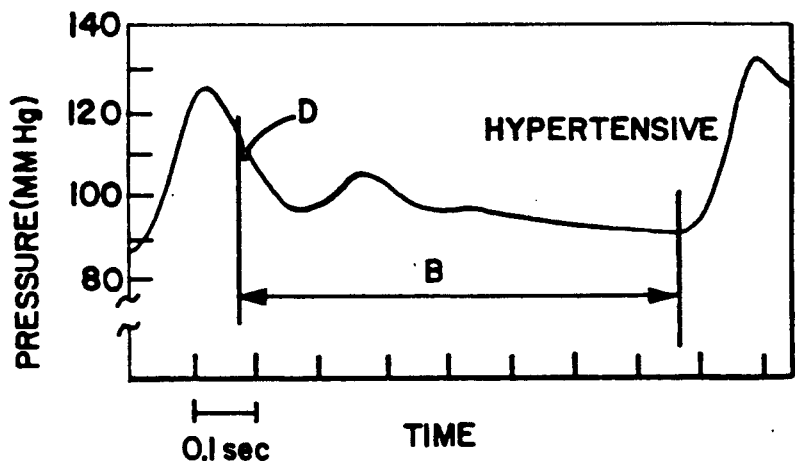
FIG. 6 is an illustrative example of typical arterial pulse contours in diseased patients.

An initialization and mode select routine 52 is provided for initializing microprocessor 14, including prompting the user to enter the date (and other desired patient information). Routine 52 further allows either the monitor mode or communication mode to be selected. If the monitor mode is selected, A/D convertor 12 is activated (54) to digitize the analog brachial pressure pulse signal generated by transducer 34 in its position in the patient's brachial artery. Referring to FIGS. 5 and 6, there are illustrated typical brachial artery pulse contours for healthy and hypertensive patients, respectively.

The present invention uses an A/D sampling rate of 200 samples/second, which is satisfactory to capture the highest frequency components of interest in the brachial pressure pulse. It shall be understood, however, that higher or lower sampling rates may be used, and that the invention is in no way limited to the 200 samples/second rate. Routine 56 provides that the artery is monitored for approximately 30 seconds, producing in the range of 25 to 60 digitized pulses, depending on the heart rate. The stream of digitized pulses are stored in RAM 22 in the form of a continuous series of periodic time dependent data byte samples, with each data byte corresponding to the instantaneous pressure of the artery.

Routine 60 is provided for acquiring a cardiac output value, which is required for calculation of impedance parameters as explained in more detail below. In the present embodiment cardiac output is input directly from keyboard 16 in liters/minute or alternatively, milliliter/second. Cardiac output may be determined by the thoracic impedance technique using for example the Minnesota Impedance Cardiograph model 30413, with the results being manually transferred to apparatus 10. Alternatively, it is contemplated that another non-invasive instrument may be used for this purpose, with the measured output being fed directly into monitor 10 through a microprocessor port. There are, of course, well-known invasive techniques for determining cardiac output.

A selection routine 20 is also provided to analyze the recorded waves and to select a group of at least six consecutive representative beats preferably of comparatively low noise content. Representative beats are identified by establishing windows of permissible heart rate and mean arterial pressure values whereby abnormally fast or slow heartbeats or high or low pressures can be rejected. The routine can thus pick the series of beats which is most representative. Where possible it is preferable that the windows be tailored to the patient, thus allowing more precise selection of representative beats.

Because only the diastolic portion of each selected beat is of interest, i.e. that part of the pressure wave which corresponds to the period of diastole in the heart, a routine 72 is provided to identify the relevant portions. When marked manually, a clinician can identify the onset of diastole by correlating to the second heart sound $S_2$, and the end of diastole by the upstroke of the following pulse. For example, in FIGS. 5 and 6 diastole is marked by the respective segments A and B. However, for the sake of simplicity the present invention uses a software analysis algorithm to predict and select the segment in each wave most probably corresponding to diastole. It is, however, important that the onset of the wave to be used occurs after the peak in the systolic wave and preferably twenty to fifty milliseconds before the dicrotic notch. Thus, routine 72 searches for the dicrotic notch (D), and marks the onset of diastole just before the location of the dicrotic notch on the wave. The end of diastole in the waveform is easily located by finding the upstroke of the next pulse. Alternatively, device 10 could include means for digitizing an analog signal representing the heart sounds, and software for identifying the second heart sound $S_2$ and correlating it to the digitized arterial waveform to identify the onset of diastole. With the relevant segments marked the data for each pulse can be analyzed to reveal the vascular impedance properties of the patient.

As referred to above, the modified Windkessel model of the arterial system is used in the pulse contour analysis of the present invention. As described above, the model includes components $P_1$, $P_2$, $C_1$, $C_2$, L and R in which:

$C_1$ = proximal compliance (ml/mm Hg)
$C_2$ = distal compliance (ml/mm Hg)
L = inertance (mm Hg/ml/s$^2$)
$P_1$ = proximal arterial pressure (mm Hg)
$P_2$ = brachial artery pressure (mm Hg)
R = peripheral resistance (dynes s cm$^{-5}$)

As taught for example by Goldwyn and Watt in Arterial Pressure Pulse Contour Analysis Via a Mathematical Model for the Clinical Quantification of Human Fascular Properties, I.E.E.E. Trans. Biomed. Eng. 1967; 14:11:-17, the disclosure of which is hereby incorporated by reference herein, $P_2$ of the modified Windkessel model may be represented by the third order equation:

$$P_2(t) = A_1 \exp(-A_2 t) + A_3 \exp(-A_4 t) \cos(A_5 t + A_6),$$
wherein:

$$C_1 = \frac{mn - p}{mp} \cdot \frac{1}{R}$$

$$C_2 = \frac{1}{m} \cdot \frac{1}{R}$$

$$L = \frac{m^2 R}{mn - p}$$

wherein:

$$m = A_2 + 2A_4$$

$$n = 2A_2 A_4 + A_4^2 + A_5^2$$

and $$p = A_2(A_4^2 + A_5^2)$$

Thus, knowing R, which can be calculated from cardiac output and mean arterial pressure as follows:

$$R = \frac{\text{mean arterial pressure}}{\text{cardiac output}},$$

$C_1$, $C_2$ and L are readily calculated.

To accomplish the above, software 50 includes routine 80-82, which comprises a modified Gauss-Newton parameter-estimating algorithm as for example referenced by Watt and Burrus in their paper entitled "Arterial Pressure Contour Analysis for Estimating Human Vascular Properties", Journal of Applied Physiology, 1976; 40:171-176, the disclosure of which is hereby incorporated herein by reference. Routine 80-82 calculates the optimal values for coefficients $A_1$-$A_6$, using the measured brachial arterial pressure as $P_2(t)$. The algorithm uses an iterative approach which preferably provides fast convergence. The algorithm used in routine 80-82 includes certain modifications. An automatic stopping procedure is included to stop iteration when an acceptable error level in the curve fitting threshold is reached or when convergence slows below a preset threshold. Also, when the process begins to diverge it returns to the previous best case. The routine also includes a weighted iteration interval to improve convergence.

Once the coefficients $A_1$-$A_6$ are established for each pulse contour, the coefficients are used at routine 84 to calculate the $C_1$, $C_2$ and L vascular impedance parameters for each pulse contour. $C_1$, $C_2$ and L are all calculated in accordance with the formulas given above. Once calculated for each pulse contour the calculated values are average at routine 86, producing mean values more reliable for accuracy than any individual values. It shall be understood, however, that the averaging process is not essential. For instance, a median value could be selected for use if desired. After calculation, the distal compliance parameter $C_2$ is stored in RAM 22 according to date, preferably in chronological order with parameters determined on previous days. Monitor 10 is further operative to analyze the acquired distal compliance values in order to indicate the likelihood of unlikelihood of the hypertensive disease condition in the patient being monitored. In the present embodiment, diagnostic analyses are performed at the end of each monitoring operation. It is contemplated, however, that diagnosis could be initiated under independent keyboard 16 control if desired. The first diagnostic test performed is preferably a threshold test, performed at routine 100 to determine whether the distal compliance ($C_2$) value is above, below or in between one or more threshold values which are preferably predetermined and stored in RAM 22 and RAM 20. Routine 100 can be programmed in accordance with the diagnostic methods outlined hereinabove.

Optionally, routines 102 and 110 are also provided for diagnostic purposes, and provide for analyzing distal compliance values accumulated over time to determine the slope or trend of the values over time, for instance over a month or year. Thus, routines 102 and 110 can anticipate a trend toward the hypertensive disease condition as indicated by diminishing distal compliance and evaluate the significance or abruptness of the trend. Conversely, a trend toward improved distal compliance can also be determined, indicating an improvement of the hypertensive disease condition, as may result from beneficial therapy. Routine 110 also optionally includes diagnostic logic to evaluate the interrelationship between $C_2$ values and the slope of the values, or other desirable criteria, to provide more sophisticated diagnosis.

Routine 120 is provided to indicate via display 18 the value of the $C_2$ parameter determined by the software, and the result of the threshold tests provided at routine 100, whereby, for instance, when distal compliance falls below the selected threshold value, a likelihood of the hypertension disease condition is indicated. Routine 140 is also provided to report (140) the analysis results on an optional printer 42.

In case the diagnosis indicates a dangerous condition as may be indicated by an extremely low $C_2$ value or a dangerous trend as may be indicated for example by a severe distal compliance slope a warning routine 130 is provided to cause monitor 10 to produce a warning indication, either through display 18, or in a printed report (140) to optional printer 42.

Monitor 10 also includes communications capability, whereby accumulated $C_2$ data (or, if desired other stored vascular parameters) may be communicated to further computer equipment 44 in a clinic or hospital, such as a personal computer or minicomputer. Accordingly, monitor 10 may be used by a patient at home with measured and stored parameters particularly $C_2$, being transmitted back to a treating hospital or clinic for review or for further analysis. For this purpose software 50 provides a communications mode including routines 145 and 146, which provide for establishing a communication link with a remote system and for downloading selected information including accumulated $C_2$ values.

As shown in FIG. 1, a clinic or hospital computer 44 is provided to communicate with monitor 10 using a standard modem-telephone link. FIG. 7 illustrates in diagrammatic form the software 150 provided for clinic computer 44. A routine 152 is provided for establishing the communication link with monitor 10. Computer 44 preferably includes an auto-answer modem so that monitor 10 may establish communication therewith with a minimum of effort. Data acquisition routine 154 is provided to receive $C_2$ values and other desired data which may be stored in RAM 22, such as cardiac output, mean arterial pressure, $C_1$, L and slope data.

Routine 156 is provided to evaluate $C_2$ and, optionally, other vascular properties. Routine 156 includes all the capabilities described with respect to monitor 10 (routines 100, 102, 110), and preferably more sophisticated analysis techniques which would take into account other known patient data, such as the patient's medical history. At a minimum, routine 156 provides for a printed report of acquired $C_2$ values which may be reviewed by the treating personnel or physician. Finally, a routine 158 is provided to suggest therapy strategy based on the results of evaluation 156.

Although the invention has been described here in its preferred form, those skilled in the art will readily recognize that many modifications and changes may be made thereto without departing from the spirit and scope of the claims appended hereto.

I claim:

1. A method for diagnosing the hypertensive disease condition in a human patient comprising the steps of:
    a) determining for said patient a measure of distal compliance of the patient's vasculature;
    b) diagnosing said patient as having the hypertensive disease condition according to, at least in part, if said measured distal compliance is below a first predetermined diagnostic threshold; and
    c) diagnosing said patient as not having the hypertensive disease condition according to, at least in part, if said measured distal compliance is above a second predetermined diagnostic threshold.

2. A method for treating a patient with borderline hypertension comprising the steps of:
    a) determining for said patient a measure of the distal compliance of the patient's vasculature;
    b) administering medications known to raise said measured distal compliance value according to, at least in part, if said measured distal compliance is below a predetermined diagnostic threshold; and
    c) identifying said patient as one not likely to benefit from administration of medication which raise distal compliance according to, at least in part, if the measured distal compliance is above said predetermined diagnostic threshold.

3. A method for diagnosing the hypertensive disease condition in a patient comprising the steps of:
    a) determining for said patient a measure of distal compliance of the patient's vasculature; and
    b) diagnosing the hypertensive disease condition for said patient according to, at least in part, if said measured distal compliance is below a predetermined diagnostic threshold.

4. A method for early detection of the onset of the hypertensive disease condition in a patient comprising the steps of:
    a) determining for said patient a measure of the distal compliance of the patient's vasculature;
    b) repeating step a) over a period of time and charting the measured distal compliance values obtained thereby; and
    c) diagnosing a movement toward the onset of the hypertensive disease condition according to, at least in part, if said charted distal compliance is trending downwardly.

5. A method for monitoring a progress of the hypertensive disease condition comprising the steps of:
    a) determining for said patient a measure of the distal compliance of the patient's vasculature;
    b) repeating step a) over a period of time and charting the measured distal compliance; and
    c) diagnosing the progress of the hypertensive disease condition based on said charted distal compliance, said progress being diagnosed as unchanged according to, at least in part, if said distal compliance stays substantially unchanged over time, worsening according to, at least in part, if said distal compliance decreases over time, and improving according to, at least in part, if said distal compliance increase over time.

6. A method according to claims 1, 2, 3, 4, or 5 wherein said measure of distal compliance is the parameter $C_2$ of the modified Windkessel model.

7. A method according to claim 1 wherein said measure of distal compliance is the parameter $C_2$ of the modified Windkessel model and said first diagnostic threshold is about 0.05 mm/ml Hg.

8. A method according to claim 7 wherein said second predetermined diagnostic threshold is about 0.08 mm/ml Hg.

9. A method according to claim 3 wherein said measure of Windkessel model and said distal compliance is the parameter $C_2$ of the modified diagnostic threshold is about 0.05 mm/ml Hg.

10. A method according to claim 1 wherein said measure of distal compliance is the parameter $C_2$ of the modified Windkessel model and said first and second predetermined diagnostic thresholds are about 0.05 mm/ml Hg.

11. A method according to claim 1 wherein said measure of distal compliance is the parameter $C_2$ of the modified Windkessel model and said first and second predetermined diagnostic thresholds are about 0.08 mm/ml Hg.

12. A method according to claim 2 wherein said measure of distal compliance is the parameter $C_2$ of the modified Windkessel model and said predetermined diagnostic threshold is about 0.05 mm/ml Hg.

13. A method according to claim 2 wherein said measure of distal compliance is the parameter $C_2$ of the modified Windkessel model and said predetermined diagnostic threshold is about 0.08 mm/ml Hg.

14. A method according to claim 3 wherein said measure of distal compliance is the parameter $C_2$ of the modified Windkessel model and said predetermined diagnostic threshold is about 0.08 mm/ml Hg.

15. A method for diagnosing and treating the hypertensive disease condition in a human patient comprising the steps of:
    a) determining for said patient a measure of distal compliance of the patient's vasculature;
    b) diagnosing said patient as having the hypertensive disease condition and administering treatment for said condition, according to, at least in part, the value of said measured distal compliance; and
    c) diagnosing said patient as not having the hypertensive disease condition according to, at least in part, the value of said measured distal compliance.

16. A method for treating a patient with borderline hypertension comprising the steps of:
    a) determining for said patient a measure of the distal compliance of the patient's vasculature; and
    b) administering a treatment program to reduce the blood pressure of said patient according to, at least in part, the value of said measure distal compliance.

17. The method according to claim 16 wherein said treatment program includes administering medications.

18. A method for diagnosing and treating the hypertensive disease condition in a patient comprising the steps of:
    a) determining for said patient a measure of distal compliance of the patient's vasculature;

b) diagnosing the hypertensive disease condition for said patient according to, at least in part, the value of said measured distal compliance; and c) administering a treatment program to reduce the blood pressure of a patient diagnosed as having the hypertensive disease condition.

19. The method according to claim 18 wherein said treatment program includes administering medications.

20. A method for early detection of the onset of the hypertensive disease condition in a patent and for treatment thereof comprising the steps of:

a) determining for said patient a measure of the distal compliance of the patient's vasculature;

b) repeating step a) over a period of time and charting the measured distal compliance values obtained thereby;

c) diagnosing a movement toward the onset of the hypertensive disease condition according to if, at least in part, said charted distal compliance is trending downwardly; and d) administering a treatment program to delay or prevent the onset of the hypertensive disease condition if a movement toward the onset of the hypertensive disease condition is diagnosed.

21. The method according to claim 20 wherein said treatment program includes administering medications.

22. A method according to claims 15, 16, 17, 18, 19, 20 or 21 wherein said measure of distal compliance is the parameter $C_2$ of the modified Windkessel model.

23. A method according to claim 15, 16 or 18 wherein said measure of distal compliance is the parameter $C_2$ of the modified Windkessel model and said value is compared against a diagnostic threshold of about 0.05 mm/ml Hg to identify patients as having the hypertensive disease condition.

24. A method according to claim 18 or 20 wherein said treatment program included the administration of medications to improve the distal compliance of the patient's vasculature.

25. A method according to claims 15, 16, or 18 wherein said measure of distal compliance is the parameter $C_2$ of the modified Windkessel model and said value of said measured distal compliance is compared against a diagnostic threshold of about 0.08 mm/ml Hg to identify patients as having the hypertensive disease condition.

26. A method according to claim 16 wherein said measure of distal compliance is the parameter $C_2$ of the modified Windkessel model and said value of said measured distal compliance is compared against a diagnostic threshold of about 0.12 mm/ml Hg to identify the borderline patients as having the hypertensive disease condition and being a good candidate for said treatment program.

* * * * *

UNITED STATES PATENT AND TRADEMARK OFFICE
CERTIFICATE OF CORRECTION

PATENT NO. : 5,054,493

DATED : October 8, 1991

INVENTOR(S) : Cohn, et al.

It is certified that error appears in the above-identified patent and that said Letters Patent is hereby corrected as shown below:

Column 4, line 22, after "and" insert--who--.

Column 4, line 22, delete "would have had anormal" and insert therefore--have a normal--.

Column 5, line 62 "1...·6" should read therefore --1....6--.

Column 5, line 68, delete "arteriole" and insert --arterial--.

Column 8, line 48, after "as" insert--a threshold for clinical use is to some degree a matter of--.

Column 9, line 16, delete "part" and insert thereto--port--.

Column 10, line 5, delete first occurrence of ",".

Column 10, line 60, after "in" insert--"--

Column 10, line 63, delete "Fascular" and insert--Vascular--

Column 10, line 63, after "Properties," insert--"--.

Column 11, line 24, after "pressure" insert--,--.

UNITED STATES PATENT AND TRADEMARK OFFICE
CERTIFICATE OF CORRECTION

PATENT NO. : 5,054,493
DATED : October 8, 1991
INVENTOR(S) : Cohn, et al.

It is certified that error appears in the above-identified patent and that said Letters Patent is hereby corrected as shown below:

Column 11, line 62, delete "of" and insert —or—.

Signed and Sealed this

Twentieth Day of July, 1993

Attest:

MICHAEL K. KIRK

Attesting Officer        Acting Commissioner of Patents and Trademarks